United States Patent [19]
Vaillancourt

[11] Patent Number: 5,669,891
[45] Date of Patent: Sep. 23, 1997

[54] FEMALE LUER CONNECTOR

[76] Inventor: Vincent L. Vaillancourt, 14 Bunyan Dr., Livingston, N.J. 07039

[21] Appl. No.: 622,867

[22] Filed: Mar. 29, 1996

Related U.S. Application Data

[63] Continuation-in-part of Ser. No. 365,900, Dec. 29, 1994, Pat. No. 5,509,912, which is a continuation-in-part of Ser. No. 328,045, Oct. 24, 1994, Pat. No. 5,514,116.

[51] Int. Cl.⁶ ........................................ A61M 5/00
[52] U.S. Cl. .............................. 604/283; 604/88; 604/411
[58] Field of Search ........................ 604/283, 280, 604/905, 175, 411, 414, 85, 86, 88, 91, 264

[56] References Cited

U.S. PATENT DOCUMENTS

| | | | |
|---|---|---|---|
| 4,645,494 | 2/1987 | Lee et al. | 604/175 |
| 4,683,916 | 8/1987 | Raines | 137/854 |
| 5,306,243 | 4/1994 | Bonaldo | 604/86 |
| 5,342,326 | 8/1994 | Peppel | 604/284 |
| 5,380,306 | 1/1995 | Brinon | 604/244 |

FOREIGN PATENT DOCUMENTS 9311828  6/1993  WIPO.

*Primary Examiner*—John D. Yasko
*Attorney, Agent, or Firm*—McAulay Fisher Nissen Goldberg & Kiel LLP

[57] ABSTRACT

The female luer connector is constructed with a floating hollow needle. The needle is mounted within a collapsible tubular member with the distal end of the needle fitted into a recess of a septum integral with the collapsible member. The hollow needle is free to move transversely relative to the housing and a rigid tubular part of the connector. Eccentricity of the septum relative to the rigid tubular part is avoided and insertion of a male connector automatically aligns the septum and needle with the longitudinal axis of the rigid tubular part. Various arrangements are provided for anchoring the flange of the collapsible tubular part between the housing and rigid part in seal-tight manner.

21 Claims, 3 Drawing Sheets

FEMALE LUER CONNECTOR

This is a continuation-in-part application of U.S. patent application Ser. No. 08/365,900 filed Dec. 29, 1994 now U.S. Pat. No. 5,509,912 which is a continuation-in-part application of application Ser. No. 08/328,045 filed Oct. 24, 1994 now U.S. Pat. No. 5,514,116.

This invention relates to a connector. More particularly, this invention relates to a female luer connector for intravascular or urological use.

Heretofore, various types of connectors have been known, for example, for intravascular and urological use, wherein a hollow needle is disposed within a collapsible tube having a rubber septum at a distal end positioned coaxially of the needle. Where such a connector has been made as a female luer connector, use has been made of a male luer connector or the like to engage with and to push the septum back over the needle thereby exposing the needle. During this time, the needle pierces through the septum and enters into the male luer connector thereby establishing communication therewith. Connectors employing such constructions are described in U.S. Pat. No. 5,122,123.

One of the concerns with the above types of connectors has been the possibility that repeated piercing of the septum, which is usually made of rubber, in more or less one location may allow leakage through the septum after the septum has been returned to an extended position spaced from the hollow needle. This is particularly due to the fact that the thickness of the septum is limited. As a result, the potential resistance to a high pressure is limited.

In order to minimize the concern concerning leaking, use has been made of a compression ring about the septum so that a preload is placed upon the septum in order to ensure a self-sealing of the septum after the septum has been slid off a needle when returning to an extended position.

Another concern which has arisen with respect to septum luer connectors of this type has been the potential for silvering of the septum by the needle. That is, during penetration of the septum by the hollow needle, there is a risk that a sharp needle will cut out a small silver from the male luer connector and allow the silver to pass into the blood flow of a patient. This concern can be overcome by slightly bending the tip of the needle inwardly.

Still another concern with connectors which employ a needle within a rigid tubular part is that during manufacture, the needles may not be precisely centered within the tubular part. Thus, there is almost always some misalignment at the tip of the hollow needle relative to the axis of the tubular part. As a result, where a septum is placed over the distal end of the needle, such as described in pending U.S. application Ser. No. 08/365,900 filed Dec. 29, 1994, the septum may become mis-aligned with respect to the axis of the rigid tubular part thereby becoming eccentrically aligned relative to the inside wall of the rigid tubular part. Subsequently, when a male luer connector or the like is pushed into the rigid tubular part to slide the septum along the needle to expose a pair of openings in the side of the needle, the eccentricity of the needle may exacerbate the problems of leakage and/or silvering further. In cases where a blunt needle with diametrically disposed apertures in the side is recessed in a septum, one of the apertures in the needle may have a reduction in flow therethrough because of the throttling effect brought about because the needle is closer to the wall of the rigid tubular part at that opening than at the other opening. In addition, the misalignment of the septum may allow the septum to rub against the internal wall of the rigid tubular part resulting in friction forces which may retard or prevent septum recovery when the male luer connector is removed.

Another concern which arises with various types of connectors is the concern for sterility. Accordingly, connectors, particularly of the female luer type, usually require a construction which permits sterility to be obtained either because of the types of materials used or a construction which does not have recesses in which bacteria and the like may accumulate.

Accordingly, it is an object of the invention to provide a female luer connector which is able to automatically align a needle and septum with a male luer.

It is another object of the invention to be able to mount a septum on a needle within a female luer without eccentricity therebetween.

It is another object of the invention to eliminate any risk of septum recovery within a female luer upon removal of a male luer connector.

Briefly, the invention provides a female luer connector which is comprised of a housing having a passage for a flow of fluid, a rigid tubular part which extends from the housing coaxially of the passage, a longitudinally collapsible tubular member disposed concentrically within the rigid tubular part and a septum integral with a distal end of the collapsible tubular member and having a recess disposed concentrically of the rigid tubular part.

In accordance with the invention, a hollow needle having a distal end slidably received in the recess of the septum has a proximal end unsecured to either the housing or the rigid tubular part whereby the needle is free to move transversely relative to the housing and the rigid tubular part with the septum. In this sense, the hollow needle is mounted within the rigid tubular part in a floating manner.

The needle, by residing within the septum at the distal end, is free to move in a direction normal to the axis of the needle. In this manner, when a male luer connector, or the like is attached, the hollow needle and septum are automatically aligned axially and accommodate the male luer connector in the center of the rigid tubular part of the female luer connector. In this manner, the concern for axial alignment is eliminated and normal needle manufacturing tolerances associated with making hollow needles can readily be accommodated.

Various types of seals may be used to secure the collapsible tubular member to the housing and/or rigid tubular part while maintaining the floating condition of the needle yet providing an adequate seal. By way of example, the collapsible tubular member has a radially directed flange at the proximal end which is sandwiched between the housing and the rigid tubular part. In such an embodiment, the rigid tubular part and housing may be ultrasonically sealed together after assembly in order to form a unitary structure.

In view of the manner of use of the female luer connector, it is important that the face of the septum be readily wipeable using a suitable disinfectant. To this end, the septum is disposed so as to project from the rigid tubular part to permit wiping of the face of the septum for sterilization purposes, for example, by using a suitable disinfectant. Alternatively, the face of the septum may be coated with an anti-microbial coating, for example based upon silver or a silver ion, and the like. In this case, if the surface of the septum is rendered anti-microbial, then the need to be able to wipe the face of the septum is substantially reduced, in which case, the septum may also be recessed within the rigid tubular part.

Typically, the needle has a blunt rounded distal end with a pair of diametrically disposed openings adjacent the distal end for the flow of fluid therethrough. These openings may be sealingly received in the recess of the septum in an extended position of the collapsible member or may be disposed proximally in spaced relation to the recess in the septum thereby being exposed to any fluid within the collapsible tubular member.

The female luer connector may also include a spring disposed concentrically about the needle within the collapsible member for biasing the collapsible member into an extended position relative to the needle.

The needle is provided with a radially directed flange at the proximal end which abuts the housing so as to be in sliding contact with the housing. The needle also has a longitudinal passage in communication with the passage in the housing in order to convey fluid therebetween. Typically, the collapsible member sealingly abuts the flange of the needle at the proximal end of the collapsible member.

In one embodiment, at least one of the housing and the rigid part has at least one projection for engaging in and deforming a portion of the flange of the collapsible member in order to secure the flange in place.

Other embodiments of the female luer connector may also be provided similar to those embodiments described in the parent application, Ser. No. 08/365,900. For example, in one embodiment of the septum may be provided with a slit to facilitate the passage of the hollow needle. In another embodiment, the septum may be of solid construction, that is, without a slit. In this latter embodiment, the needle may be provided with a spike end or the like which is able to pierce through the septum.

The septum may be made of any suitable material and preferably of rubber.

In one embodiment, the opening in the needle is sealingly received within the recess of the septum for example with an interference fit between the needle and the septum. In this embodiment, any fluid seeking to escape from the needle must therefore pass through the opening in the side of the needle and must force the inner wall of the septum to expand sufficiently to allow the fluid to pass between the needle and septum to the outside of the septum. By controlling the amount of the interference fit between the septum and the needle, the leakage pressure can be increased or decreased.

In another embodiment, the opening in the needle may be partially received in sealed relation within the recess of the septum whereas in another embodiment, the opening may be spaced longitudinally from the recess of the septum.

In still another embodiment, a compression ring may be concentrically mounted on the septum in order to circumferentially compress the wall of the septum. The compression ring thus serves to significantly increase the leakage pressure at relatively low interference fits. By encapsulating the septum in the compression ring, it becomes virtually impossible for the septum to flow, i.e. to relieve the compressive force thereon. As a result, the initial sealing characteristics may be retained over a relatively long period of time.

In another embodiment, the septum is provided with two internal annular portions in order to slidably receive the needle in sealed relation for different purposes. For example, the septum includes a first annular portion for slidably receiving the distal end of the needle for storage purposes and a second annular portion farther along towards the distal end of the septum. Thus, over time, any set in the material of the rubber septum due to the circumferential expansion of the septum in this area does not interfere with the subsequent need to have a reliable seal when in use.

In still another embodiment, an inner annular wall extends from the septum in spaced concentric relation to the outer wall to receive the distal end of the needle in seal tight relation. In addition, the opening of the needle may be disposed within the plane of the inner annular wall or may be disposed completely outside the inner annular wall or only partially within and partially outside the inner annular wall. In this embodiment, where the opening is not completely sealed over, fluid may flow through the needle into the surrounding tubular portion and into the space between the two concentric walls. In this way, the pressure of the fluid within the collapsible tubular part serves to increase the sealing pressure on the distal end of the needle via the inner wall. One advantage of this embodiment is that the same seal leakage properties can be obtained as in the other embodiments with much less of an interference fit between the needle and the rubber septum.

It has been found that the collapsible tubular portion longitudinally elongates under an internal pressure. When the elongation of the tubular portion is sufficient that the needle no longer is fully engaged with the septum, the connector may begin to leak. Specifically, leakage takes place through the slit in the septum. Accordingly, in another embodiment, a means is provided for preventing longitudinal stretching of the collapsible tubular portion under an internal pressure to a degree at which the septum is no longer maintained on the needle in sealed relation. By way of example, such a means includes an internal shoulder on the rigid tubular part of the connector and an external annular ring on the collapsible tubular portion for abutting the shoulder in an extended position of the collapsible tubular portion, i.e. in a stretched condition. In this way, the pressure required to initiate leakage is substantially increased. In addition, upon removal of the internal pressure, the septum retracts unto the needle so that the connector behaves in the normal manner.

The connector may be constructed so that the septum projects slightly beyond the tubular housing part. In this position, the face of the septum is exposed so that the face can be wiped prior to use with a suitable material to remove and/or kill bacteria. Also, the septum may be positioned flush with the housing part. In the alternative, a coating or a deposit, such as of silver or anti-microbial material may be applied on the face of the septum. In this latter case, there should be no need to swab the septum prior to use.

These and other objects and advantages of the invention will become more apparent from the following detailed description taken in conjunction with the accompanying drawings wherein.

Figure 1:
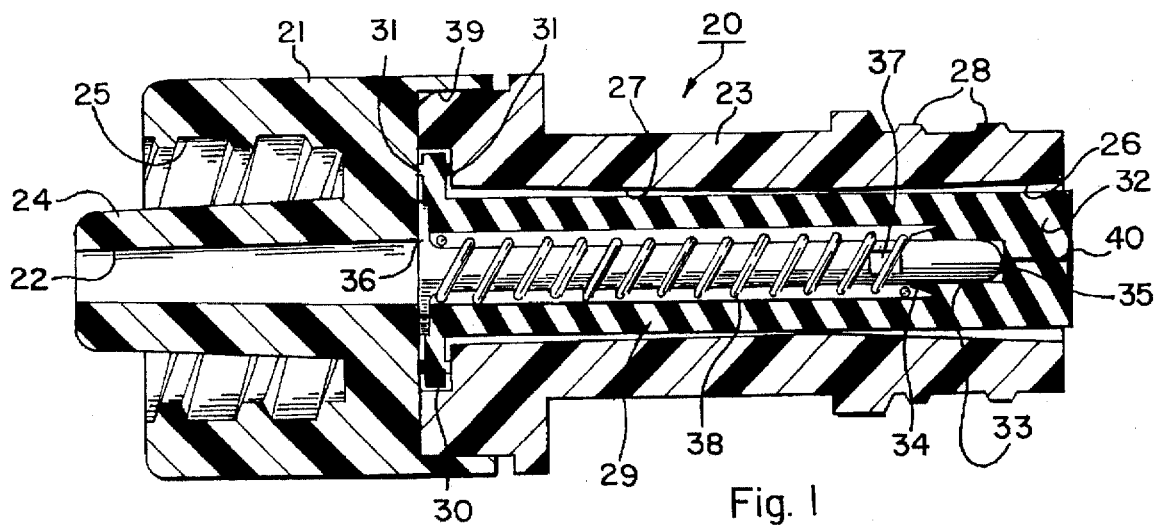
FIG. 1 illustrates a cross-sectional view of a female luer connector constructed in accordance with the invention.

Referring to FIG. 1, the female luer connector 20 is constructed with a housing 21, for example of plastic material, having an axial passage 22 for a flow of fluid and a rigid tubular part 23 extending coaxially from the housing 21. The housing 21 also has an integral tubular part 24 about the passage 22 which is concentrically surrounded by an internally threaded portion 25 of the housing 21 to form a male luer connection and thereby threadably receive a luer connector on an IV line or the like (not shown). Alternatively, the female luer connector 20 may form part of a Y-site, a T-connector or may be attached to an infusion bag. Also, the connector 20 may form part of an entrance port on a blood line (not shown).

As indicated in FIG. 1, the rigid tubular part 23 has a distal portion 26 of decreasing inner diameter in a proximal direction as well as a proximal portion 27 of increasing inner diameter in the proximal direction. The tapered distal portion 26 is of conventional shape so as to receive a male luer connector (not shown) as is known.

Figure 11:
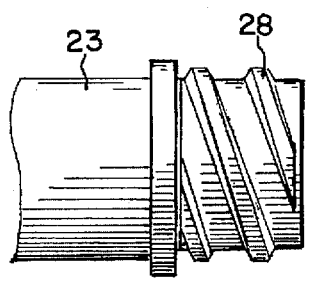
FIG. 11 illustrates the use of a thread on the rigid tubular part for securing a male luer connector in place.

The rigid tubular part 23 is also provided with means 28 in the form of an external thread (see FIG. 11) to secure a male luer connector in place.

Referring to FIG. 1, the female luer connector 21 also employs a longitudinally collapsible tubular member 29 which is disposed concentrically within the rigid tubular part 23. This tubular member 29 has a radial flange 30 at the proximal end which is sandwiched between the housing 21 and the rigid tubular part 23 so as to be secured to the rigid tubular part 23. As indicated, the flange 30 has an annular protuberance 31 on each side which abuts the respective housing 21 and rigid tubular part 23 in deformed manner so as to form seals therebetween. During assembly, the flange 30 of the collapsible tubular member 23 is positioned between the housing 21 and rigid tubular part 23 and the housing 21 and tubular part 23 are brought together to deform the protuberances 31. At the same time, the housing 21 and rigid part 23 are ultrasonically welded together to form a unitary construction. In this respect, the housing 21 and rigid part 23 are made of compatible plastic materials.

The female luer connector 20 also has a septum 32 integral with a distal end of the collapsible tubular member 29. This septum 32 has an internal recess 33 disposed concentrically of the rigid tubular part 23. In addition, in this embodiment, the septum 32 has a proximally extending annular wall 34 coaxially of the recess 33. As illustrated, this annular wall 34 is radially spaced from the collapsible member 29 to define an annular gap therebetween.

The septum 32 projects slightly beyond the rigid tubular part 23 to permit wiping of the face of the septum 32 for sterilization purposes, for example with use of a suitable disinfectant. Alternatively, the flat face of the septum 32 may be coated or otherwise rendered anti-microbial by the use of silver or silver ion, or the like. If the face of the septum 32 is rendered anti-microbial, then the need to be able to wipe the septum is substantially reduced. Alternatively, where the septum is provided with an anti-microbial coating on the face, the septum 32 may be recessed within the rigid tubular part 23 by a slight distance.

A hollow needle 35 is slidably received in the recess 33 of the septum 32 and has a radially directed flange 36 at the proximal end which is unsecured to the housing 21 or to the rigid tubular part 23. That is to say, the needle 35 is free to move transversely relative to the housing 21 and the rigid tubular part 23 with the septum 32. As illustrated, the flange 36 of the needle abuts the housing 21 and is disposed between the flange 30 of the collapsible member 29 and the housing 21 in a sealed manner. The needle 35 also has a pair of diametrically disposed openings 37 (only one of which is shown) adjacent a blunt rounded distal end. In the embodiment illustrated in FIG. 1, the openings 37 are spaced proximally from the recess 33 and the annular wall 34. In other embodiments, the openings 37 may be disposed completely within the recess 33 or may be disposed partially within the recess 33 or annular wall 34.

The mounting of the needle 35 in the recess 33 of the septum 32 is such that any transverse movement of the septum 33 causes a transverse movement of the floating needle 35.

A spring 38 is disposed concentrically about the length of the needle 35 within the collapsible member 29 for biasing the collapsible member 29 into an extended position, as shown in FIG. 1, relative to the needle 35.

By way of example, one technique for assembling the female luer connector 20 is as follows:

First, the spring 38 is slid over the needle 35 and the needle 35 is then inserted into the collapsible tubular member 29 so that the distal end of the needle 35 slides into the recess 33 of the septum 32. In this respect, the needle 35 and recess 33 are sized so that the distal end of the needle 35 is received in an interference fit manner. Next, this resulting unit is mounted on the housing 21 with the flange 36 of the needle 35 abutting the housing 21. Thereafter, the rigid tubular part 23 is slid over the unit and into a recess 39 of the housing 21. The relative sizes of the components is such that insertion of the tubular part 23 into the recess 39 of the housing 21 with a slight compressive force deforms the protuberances 31 on the flange 30 of the collapsible part 29 to effect a seal between the respective parts. The housing 21 and rigid part 23 are then ultrasonically welded together to form a unitary construction.

In this manner, the collapsible tubular member 29 is firmly anchored in place.

As illustrated in FIG. 1, the septum 32 may also be provided with a slit 40 as is known to facilitate passage of the septum 32 over the distal end of the needle 35 when in use.

Figure 2:
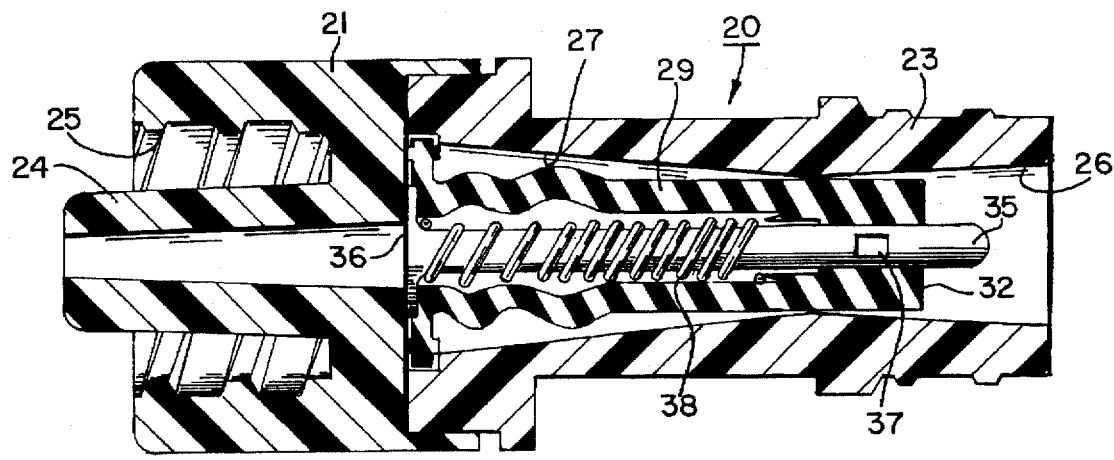
FIG. 2 illustrates a cross-sectional view similar to FIG. 1 with the collapsible tubular member in a partially collapsed position.
Figure 3:
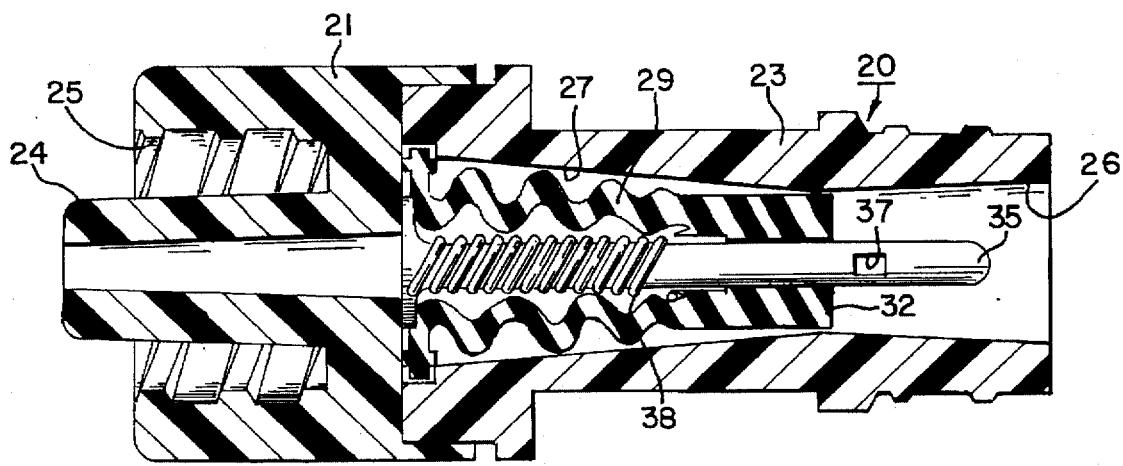
FIG. 3 illustrates a cross-sectional view similar to FIG. 1 with the collapsible tubular member in a fully collapsed position.

Referring to FIG. 2, when in use, a male luer or similar structure (not shown) is inserted into the rigid tubular part 23. At this time, the collapsible tubular member 29 begins to collapse in an accordion-type manner. At the same time, the blunt rounded distal end of the needle 35 passes through the septum 32 so as to communicate with the male luer. Continued penetration of the male luer into the rigid part 23 causes a further collapsing of the collapsible member 29, for example into a condition as shown in FIG. 3. In this collapsed position, the openings 37 of the needle become exposed to communicate with the male luer (not shown). A fluid flow may then take place through the openings 37.

As also indicated in FIG. 3, the spring 38 is compressed. Thus, when the male luer (not shown) is withdrawn from the rigid tubular part 23, the spring 38 biases the septum 32 back into the extended position shown in FIG. 1.

When the male luer connector is attached, the hollow needle 35 and septum 32 are automatically aligned axially and accommodate the male luer (not shown) in the center of the rigid tubular part 23. Further, since the needle 35 is not secured to the housing 21, any misalignment of the septum 32 within the rigid part 23 can be eliminated when the male luer penetrates into the rigid part 23. Further, when the male luer is removed, the centered septum 32 is readily biased by the spring 38 into the extended position without coming into frictional contact with the internal wall of the rigid wall 23 to the extent that frictional forces would retard or prevent septum recovery.

Figure 4:
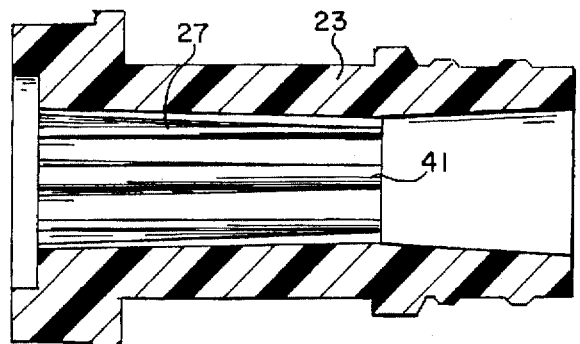
FIG. 4 illustrates a cross-sectional view of the rigid tubular part of the connector of FIG. 1.

Referring to FIG. 4, the proximal portion 27 of the rigid part 23 may be provided with a plurality of longitudinal ribs or splines 41 to facilitate extension of the collapsible member 29 (see FIG. 3) into the extended position of FIG. 1. In this respect, the ribs 41 provide relatively small surfaces which are contacted by the accordion-pleated collapsible member. Thus, the frictional forces between the pleats of the collapsed member 29 and the rigid part 23 are reduced.

Figure 5:
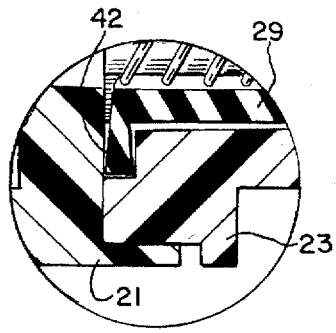
FIG. 5 illustrates a modified embodiment for anchoring the collapsible tubular member in place.

Referring to FIG. 5 wherein like reference characters indicate like parts as above, the means for anchoring the collapsible member 29 in place may employ a flange 42 on the collapsible member 29 which thickens in the radially outward direction. Such a thickened flange is then deformed in part when the rigid part 23 is secured to the housing 21.

Figure 6:
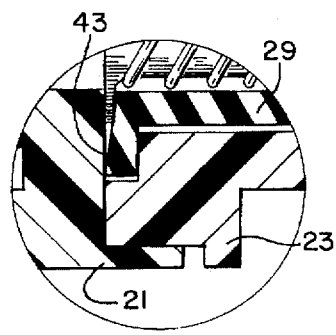
FIG. 6 illustrates a modified anchoring arrangement for the collapsible tubular member in accordance with the invention.

Referring to FIG. 6 wherein like reference characters indicate like parts as above, the thickened flange 43 of the collapsible member 29 may be thickened in only one direction. That is to say, one wall of the flange 43 lies flush against the rigid part 23 while the opposite wall is tapered relative to the housing 21. Again, when the rigid part 23 is secured to the housing 21, the flange 43 is compressively deformed at the outer periphery to effect a seal.

Figure 7:
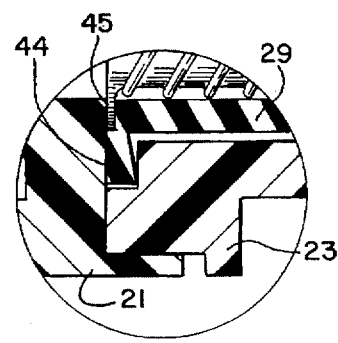
FIG. 7 illustrates a further modified anchorage for the collapsible tubular member.

Referring to FIG. 7 wherein like reference characters indicate like parts as above, the flange 44 of the collapsible member 29 may have an annular shoulder 45 facing the housing 21 and a tapered surface facing the rigid part 23.

Figure 8:
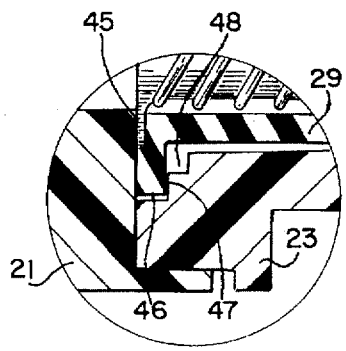
FIG. 8 illustrates a further modified arrangement for anchoring the collapsible tubular member.

Referring to FIG. 8 wherein like reference characters indicate like parts as above, the flange 46 of the collapsible member 29 may have a shoulder 45 facing the housing 21 and a flat surface 47 facing a shouldered portion 48 on the rigid part 23.

Figure 9:
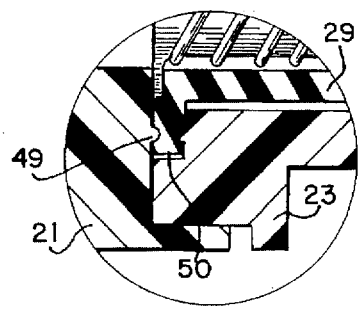
FIG. 9 illustrates a still further modification for anchoring the collapsible tubular member.

Referring to FIG. 9 wherein like reference characters indicate like parts as above, the housing 21 and rigid part 23 may have annular projections or the like 49 facing into and deforming the radial flange 50 of the collapsible member 29 in order to form a firm seal and anchorage means for the collapsible member 29.

Figure 10:
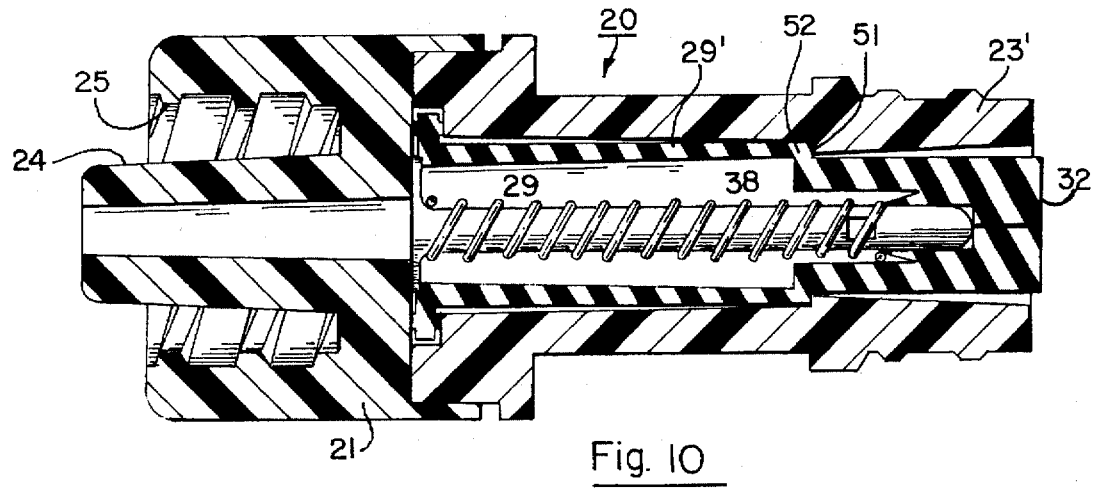
FIG. 10 illustrates a cross-sectional view of a modified rigid tubular part for preventing stretching of the collapsible tubular member beyond a predetermined point in accordance with the invention.

Referring to FIG. 10 wherein like referenced characters indicate like parts as above, in order to prevent undue stretching of the collapsible member 29, the rigid tubular part 23 has an internal shoulder 51 while the collapsible member 29' has a radially raised shoulder 52 at an intermediate point for abutting the internal shoulder 51 of the rigid part 23' to prevent stretching of the collapsible member 29' outwardly of the rigid part 23'. Such a construction has been described in parent application, Ser. No. 08/365,900 and, accordingly, no further description is believed to be necessary.

Figure 12:
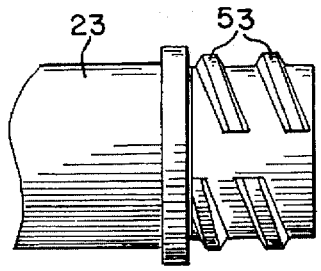
FIG. 12 illustrates a modified arrangement from FIG. 11 using an interrupted thread.
Figure 13:
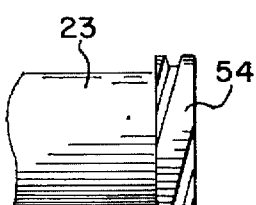
FIG. 13 illustrates a further means for securing a male luer connector in place.

Referring to FIG. 12, instead of using a continuous thread 28 on the rigid tubular part 23 to secure a male luer in place or other similar structure, use may be made of an interrupted thread for securing a male luer in place. Alternatively, as indicated in FIG. 13, a modified threaded collar 54 may be integrally formed on the rigid part 23 to receive a male luer or the like.

The various means for anchoring the collapsible member 29 in place effectively prevents the collapsible member and septum 32 from being stretched inordinately. In this respect, locking the collapsible member 29 between the housing 21 and rigid part 23 prevents leakage. For example, test pressures of up to 125 psi have been used within the connector 20 without any leakage passed the collapsible member 29.

By mounting the needle in a floating manner, there is a reduction in the cost of manufacture and time of manufacture of the connector relative to connectors which employ needles which are fixed to the housing.

The invention thus provides a female luer connector which can be manufactured at a reduced cost and with reduced time relative to connectors which employ needles which are fixed to the housing.

The invention further provides a female luer connector which can be readily wiped using a suitable disinfectant when ready for use. In addition, the invention provides a female luer connector which can be used in a sterilized manner to reduce the risk of infection.

What is claimed is:

1. A female luer connector comprising a housing having a passage for a flow of fluid;

a rigid tubular part extending from said housing coaxially of said passage;

a longitudinal collapsible tubular member disposed concentrically within said rigid tubular part, said tubular member having a proximal end secured relative to said rigid tubular part;

a septum integral with a distal end of said collapsible tubular member and having a recess disposed concentrically of said rigid tubular part; and a hollow needle having a distal end slidably received in said recess of said septum and a proximal end unsecured to said housing and said rigid tubular part whereby said needle is free to move transversely relative to said housing and said rigid tubular part with said septum.

2. A female luer connector as set forth in claim 1 wherein said collapsible tubular member includes a radially directed flange at said proximal end sandwiched between said housing and said rigid tubular part.

3. A female luer connector as set forth in claim 1 wherein said rigid tubular part has a proximal portion of increasing inner diameter in a proximal direction to accommodate expansion of said collapsible tubular member during longitudinal collapsing thereof.

4. A female luer connector as set forth in claim 1 wherein said needle has a pair of diametrically disposed openings adjacent said distal end.

5. A female luer connector as set forth in claim 4 wherein said openings are sealingly received in said recess of said septum in an extended position of said collapsible member.

6. A female luer connector as set forth in claim 1 which further comprises a spring disposed concentrically about said needle within said collapsible member for biasing said collapsible member into an extended position relative to said needle.

7. A female luer connector as set forth in claim 1 wherein said rigid tubular part has an internal shoulder and said collapsible member has a radially raised shoulder of said rigid part to prevent stretching of said collapsible member outwardly of said rigid part.

8. A female luer connector as set forth in claim 1 wherein said rigid part has an external thread on a distal end thereof.

9. A female luer connector as set forth in claim 1 wherein said rigid tubular part and said housing are ultrasonically sealed together to form a unitary structure.

10. A female luer connector as set forth in claim 1 wherein said septum includes a proximally extending annular wall coaxially of said recess and radially spaced from said collapsible member, said annular wall slidably receiving said needle therein.

11. A female luer connector as set forth in claim 10 wherein said needle has a pair of diametrically disposed openings disposed in proximally spaced relation to said annular wall.

12. A female luer connector as set forth in claim 11 which further comprises a spring disposed concentrically about said needle within said collapsible member for biasing said collapsible member into an extended position relative to said needle.

13. A female luer connector as set forth in claim 1 wherein said needle has a radially directed flange at a proximal end thereof disposed in sliding contact with said housing and a longitudinal passage in communication with said passage in said housing to convey fluid therebetween.

14. A female luer connector as set forth in claim 13 wherein said collapsible member sealingly abuts said flange of said needle at a proximal end of said collapsible member.

15. A female luer connector as set forth in claim 14 wherein said collapsible member includes a radially directed flange at said proximal end sandwiched between said housing and said rigid tubular part.

16. A female luer connector as set forth in claim 15 wherein at least one of said housing and said rigid part has at least one projection thereon engaging in and deforming a portion of said flange of said collapsible member to secure said flange in place.

17. A female luer connector as set forth in claim 1 wherein said rigid tubular part has a distal portion of decreasing inner diameter in a proximal direction.

18. A female luer connector as set forth in claim 17 wherein said rigid tubular part has a proximal portion of increasing inner diameter in a proximal direction to accommodate expansion of said collapsible tubular member during longitudinal collapsing thereof and a plurality of internally disposed longitudinally disposed ribs.

19. A female luer connector as set forth in claim 1 wherein said septum projects from said tubular part to permit wiping of a face of said septum for sterilization purposes.

20. A female luer connector as set forth in claim 1 wherein said septum has an anti-microbial coating thereon.

21. A female luer connector as set forth in claim 20 wherein said septum is recessed within said tubular part.

* * * * *